US005459161A

United States Patent [19]
Bedeschi et al.

[11] Patent Number: 5,459,161
[45] Date of Patent: Oct. 17, 1995

[54] PROCESS FOR THE PREPARATION OF SUBSTITUTED BENZOFURAN DERIVATIVES

[75] Inventors: Angelo Bedeschi, Milan; Walter Cabri, Rozzano; Ilaria Candiani, Busto Arsizio; Silvia De Bernardinis; Marcello Marchi, both of Novara, all of Italy

[73] Assignee: Farmitalia Carlo Erba S.r.l., Milan, Italy

[21] Appl. No.: 78,293

[22] PCT Filed: Dec. 27, 1991

[86] PCT No.: PCT/EP91/02512

§ 371 Date: Jun. 25, 1993

§ 102(e) Date: Jun. 25, 1993

[87] PCT Pub. No.: WO92/12147

PCT Pub. Date: Jul. 23, 1992

[30] Foreign Application Priority Data

Dec. 27, 1990 [GB] United Kingdom ............... 9028105

[51] Int. Cl.⁶ .................. A61K 31/34; A61K 31/40; C07D 307/78; C07D 207/08
[52] U.S. Cl. .................. 514/470; 514/469; 514/422; 514/403; 514/305; 514/306; 514/320; 549/462; 549/467; 549/469; 546/135; 546/138; 546/196; 548/557; 548/364.4
[58] Field of Search ............... 514/422, 470, 514/469, 422, 403, 305, 306, 320; 546/126, 135, 138, 469; 548/525, 557, 364.4; 549/462, 467, 469

[56] References Cited

U.S. PATENT DOCUMENTS

| | | | |
|---|---|---|---|
| 4,672,057 | 6/1987 | Bargiotti et al. | 514/34 |
| 4,684,629 | 8/1987 | Bargiotti et al. | 514/34 |
| 4,839,346 | 6/1989 | Bargiotti et al. | 514/34 |
| 4,987,126 | 1/1991 | Bargiotti et al. | 514/34 |
| 5,045,534 | 9/1991 | Bargiotti et al. | 514/34 |
| 5,175,173 | 12/1992 | Sun | 514/305 |
| 5,218,130 | 6/1993 | Cabri et al. | 552/201 |

FOREIGN PATENT DOCUMENTS

| | | |
|---|---|---|
| 0147044 | 7/1985 | European Pat. Off. |
| 0234872 | 9/1987 | European Pat. Off. |
| 0307172 | 3/1989 | European Pat. Off. |
| 8403281 | 8/1984 | WIPO |

OTHER PUBLICATIONS

Journal of the American Chemical Society. vol. 91, No. 23, 1969, Gaston, Pa. US, pp. 6464–6470; C. E. Castro et al.: 'Copper(I) Substitutions. Scope and Mechanism of Cuprous Acetylide Substitutions'.

(List continued on next page.)

Primary Examiner—Allen J. Robinson
Assistant Examiner—Deborah Lambkin
Attorney, Agent, or Firm—Oblon, Spivak, McClelland, Maier & Neustadt

[57] ABSTRACT

Substituted benzofuran derivatives of the formula (I):

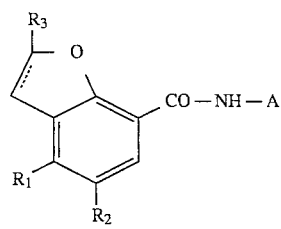

wherein one of $R_1$ and $R_2$ is hydrogen or halogen and the other is, independently, an amino group or a $C_2$–$C_4$ alkanoyl amino group; $R_3$ is hydrogen; a linear or branched $C_1$–$C_4$ alkyl, $C_1$–$C_4$ alkoxy or $C_2$–$C_4$ alkoxycarbonyl group; halogen; or phenyl unsubstituted or substituted by a $C_1$–$C_4$ alkyl group; A is a group —$(CH_2)_n$-Het wherein Het is an optionally substituted heteromonocyclic or heterobicyclic ring containing one or two nitrogen atoms, and n is zero or an integer of 1 to 3; and the symbol ..... represents a single or double bond; may be prepared by a process comprising reacting a compound of formula II:

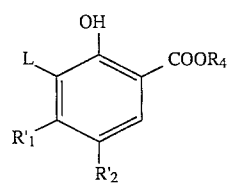

in which L is a leaving group and $R_4$ is hydrogen or a carboxy protecting group, with a compound of formula III;

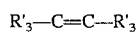

to obtain a compound of formula IV;

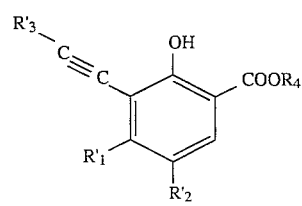

which is then cyclized to obtain a compound of formula V;

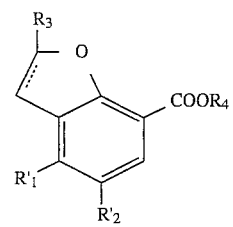

which is reacted with a compound of formula VI;

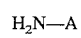

5 Claims, No Drawings

OTHER PUBLICATIONS

Synthesis of Fused Heterocycles, G. P. Ellis, Chap. 88 "Halogen and Hydroxy or Thiol" pp. 477–478, (1987).
Torii et al., *Synlett.*, pp. 515–516 (1992).
Candiani et al., *Synlett.*, pp. 269–270 (1993).
Kundu et al, *J. Chem. Comm.*, pp. 41–42 (1992).
Villemin et al, *Heterocycles,* vol. 29, pp. 1255–1261 (1989).
Iritani et al, *Tetrahedron Let.*, vol. 29, pp. 1799–1802 (1988).

PROCESS FOR THE PREPARATION OF SUBSTITUTED BENZOFURAN DERIVATIVES

This application is a 371 of PCT/EP91/02512, filed Dec. 27, 1991.

The present invention relates to a new process for the preparation of substituted benzofuran derivatives.

An object of the invention is a new process for the preparation of compounds of formula (I)

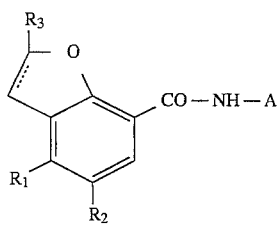

wherein
one of $R_1$ and $R_2$ is hydrogen or halogen and the other is, independently, an amino group or a $C_2$–$C_4$ alkanoyl amino group; $R_3$ is hydrogen; a linear or branched $C_1$–$C_4$ alkyl, $C_1$–$C_4$ alkoxy or $C_2$–$C_4$ alkoxycarbonyl group; halogen; or phenyl unsubstituted or substituted by a $C_1$–$C_4$ alkyl group; A is a group —$(CH_2)_n$-Het wherein Het is an optionally substituted heteromonocyclic or heterobicyclic ring containing one or two nitrogen atoms, and n is zero or an integer of 1 to 3; and the symbol .... represents a single or double bond. Also the salts and all the possible isomers of the compounds of formula (I) can be obtained by the new process of the invention. In the above formula (I) when one of $R_1$ and $R_2$ is a $C_2$–$C_4$ alkanoyl amino, it is, preferably, acetylamino or propanoylamino, in particular acetylamino. Preferably $R_1$ is amino and $R_2$ is halogen, in particular chlorine or fluorine, more particularly a chlorine. When $R_3$ is $C_1$–$C_4$ alkyl, it is, preferably, methyl or ethyl; when $R_3$ is $C_1$–$C_4$ alkoxy, it is, preferably, methoxy or ethoxy; when $R_3$ is $C_2$–$C_4$ alkoxycarbonyl, it is, preferably methoxycarbonyl; when $R_3$ is halogen, it is, preferably, chlorine; when $R_3$ is phenyl substituted by $C_1$–$C_4$ alkyl, it is preferably 4-methylphenyl. $R_3$ is preferably hydrogen. The Het moiety of the substituent A is, preferably, i) a pentatomic or hexatomic, preferably saturated, heteromonocyclic ring containing one or two nitrogen atoms, either unsubstituted or substituted by one or more $C_1$–$C_4$ alkyl groups, or by a benzyl group; or ii) a heterobicyclic, preferably saturated, ring, containing one nitrogen atom, wherein each of the condensed monocyclic ring, being the same or different, is a pentatomic or hexatomic monocyclic ring, said heterobicyclic ring being unsubstituted or substituted by one or more $C_1$–$C_4$ alkyl groups, or by a benzyl group.

Preferably n is 0 or 1. Preferably the symbol .... represents a single bond. When the Het moiety of the substituent A is a heteromonocyclic ring of the above class i), it is preferably a pyrrole or pyrazole ring, preferably saturated, optionally substituted on the nitrogen atoms; more preferably, when Het is a saturated pyrrole ring, it is, in particular, a pyrrolidine unsubstituted or substituted at the nitrogen atom by $C_1$–$C_4$ alkyl or benzyl; when Het is a saturated pyrazole ring, it is, in particular, a pyrazolidine substituted at the two nitrogen atoms by $C_1$–$C_4$ alkyl. When the Het moiety of the substituent A is a heterobicyclic ring of the above class ii), it is, preferably, a saturated azaheterobicyclic ring containing one nitrogen atom optionally substituted by $C_1$–$C_4$ alkyl or benzyl.

Specific examples of the substituent A meanings are:

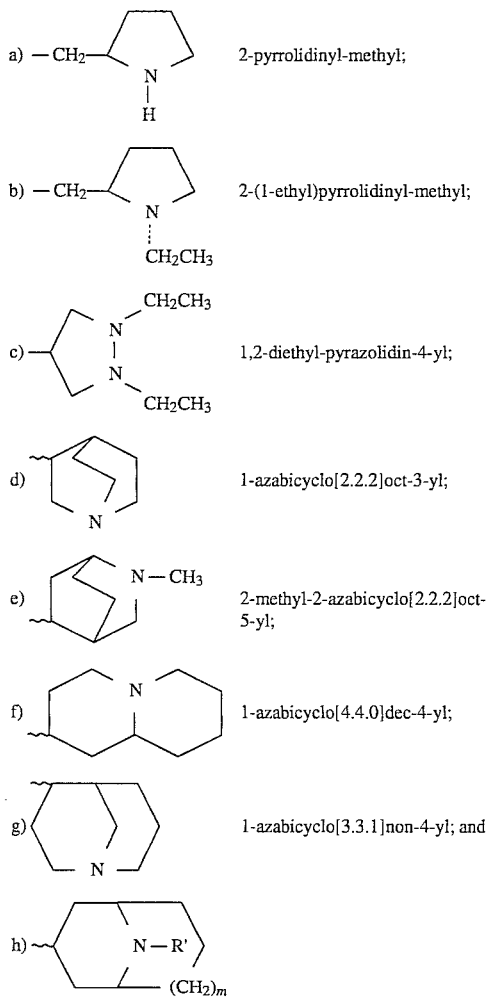

wherein
m is zero or 1 and R' is hydrogen or methyl, and
for R'=H, m=zero: 8-azabicyclo[3.2.1]oct-3-yl;
for R'=$CH_3$, m=zero: 8-methyl-8-azabicyclo[3.2.1]oct-3-yl;
for R'=H, m=1: 9-azabicyclo[3.3.1]non-3-yl;
for R'=$CH_3$, m=1: 9-methyl-9-azabicyclo[3.3.1]non-3-yl.

With reference to the azabicyclic structures in the present specification, e.g. those reported hereabove, the symbol ⋀⋀⋀ means that the azabicyclic ring may be either in the α (endo) or in the β (exo) orientation. Consequently, anywhere a formula has a substituent with a symbol ⋀⋀⋀ , the formula may represent a compound having the azabicyclic ring only in the α(endo) orientation or only in the β(exo) orientation or the formula may represent a mixture of both compounds having the azabicyclic ring in the α(endo) orientation and compounds having azabicyclic ring in the β(exo) orientation.

In particular when A in the compounds of formula (I) represents an azabicyclic ring having the structure reported above under e), f) g) or h), preferably the azabicyclic ring is in the α (endo) orientation.

Furthermore, when a chiral center is present, both individual optical isomers and their mixtures, e.g. racemates, are intended to be encompassed by the formulae of this specification. As already reported, the pharmaceutically acceptable salts of the compounds for formula (I) may also be prepared according to the process of the invention. The said salts may be salts with suitable acids, such as those with inorganic acids, e.g. hydrochloric or sulphuric acid, or with organic acids such as organic carboxylic acids, e.g., citric, tartaric, fumaric and the like, or organic sulphonic acids, e.g., methanesulphonic or ethanesulphonic acid.

Specific examples of compounds of formula (I) are the following ones, especially in the form of hydrochlorides;

1) 5-amino-N-[2-(1-ethyl)-pyrrolidinyl-methyl]-2,3-dihydrobenzo[b]furan-7-carboxamide;
2) 5-acetylamino-N-[2-(1-ethyl)-pyrrolidinyl-methyl]-2,3-dihydrobenzo[b]furan-7-carboxamide;
3) 2-methyl-4-chloro-5-amino-N-[2-(1-ethyl)-pyrrolidinyl-methyl]- 2,3-dihydrobenzo[b]furan-7-carboxamide;
4) 4-amino-5-chloro-N-[2-(1-ethyl)-pyrrolidinyl-methyl]-2,3-dihydrobenzo[b]furan-7-carboxamide;
5) 4-amino-5-chloro-N-[(1,2-diethyl)-pyrazolidin-3-yl]-2,3-dihydrobenzo[b]furan-7-carboxamide;
6) 4-acetylamino-5-chloro-N-[2-(1-ethyl)-pyrrolidinylmethyl]- 2,3-dihydrobenzo[b]furan-7-carboxamide;
7) 5-amino-N-(2-pyrrolidinyl-methyl)-2,3-dihydrobenzo[b]furan- 7-carboxamide;
8) 4-amino-5-chloro-N-(2-pyrrolidinyl-methyl)-2,3-dihydrobenzo[b]furan-7-carboxamide;
9) 4-acetylamino-N-[2-(1-ethyl)-pyrrolidinyl-methyl]-2,3-dihydrobenzo[b]furan-7-carboxamide;
10) 4-chloro-5-amino-N-[2-(1-ethyl)-pyrrolidinyl-methyl]- 2,3-dihydrobenzo[b]furan-7-carboxamide;
11) 4-amino-N-[2-(1-ethyl)-pyrrolidinyl-methyl]- 2,3-dihydrobenzo[b]furan-7-carboxamide;
12) 4-amino-5-chloro-N-(1-azabicyclo[2.2.2]oct-3-yl)-2,3-dihydrobenzo[b]furan-7-carboxamide;
13) 4-amino-5-chloro-N-(8-methyl-8-azabicyclo[3.2.1]oct-3-yl)- 2,3-dihydrobenzo[b]furan-7-carboxamide;
14) 4-amino-5-chloro-N-(9-methyl-9-azabicyclo[3.3.1.]non-3-yl)- 2,3-dihydrobenzo[b]furan-7-carboxamide;
15) 4-amino-5-chloro-N-(1-azabicyclo[4.4.0]dec-4-yl)-2,3-dihydrobenzo[b]furan-7-carboxamide;
16) 4.amino-5-chloro-N-(1-azabicyclo[3.3.1]non-4-yl)-2,3-dihydrobenzo[b]furan-7-carboxamide.
17) 4-amino-5-chloro-N-(2-methyl-2-azabicyclo[2.2.2.]oct-5-yl)- 2,3-dihydrobenzo[b]furan-7-carboxamide;

the compounds 12) to 17) being either in the exo or in the endo configuration, preferably in the endo configuration. The structural formulae of the above listed compounds, according to their progressive number, are the following:

1) 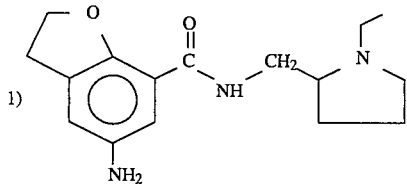

-continued

2) 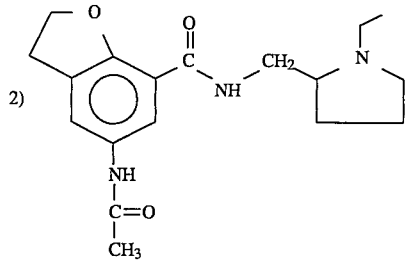

3) 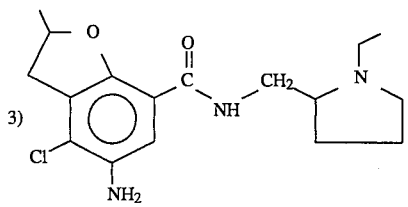

4) 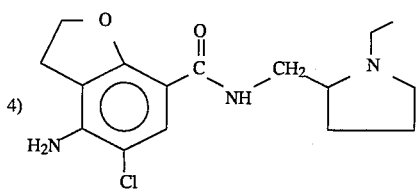

5) 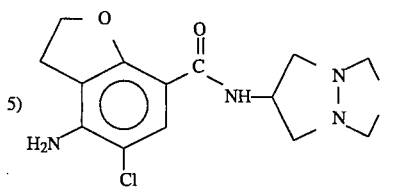

6) 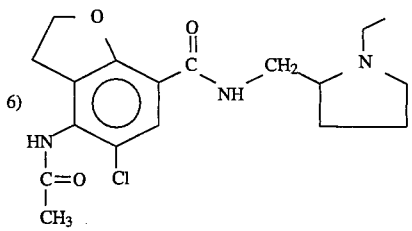

7) 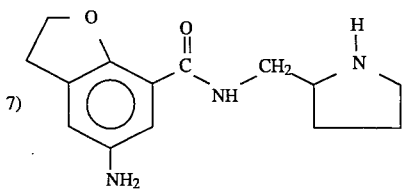

8) 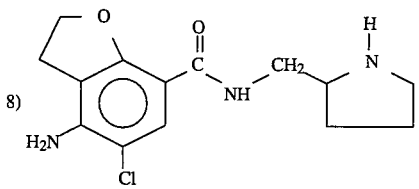

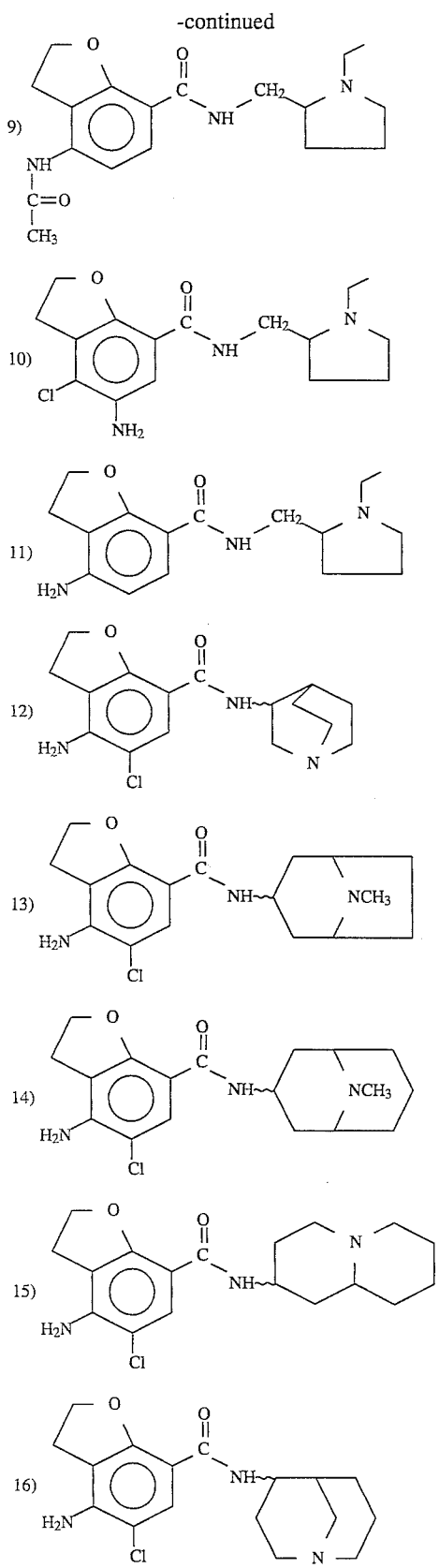

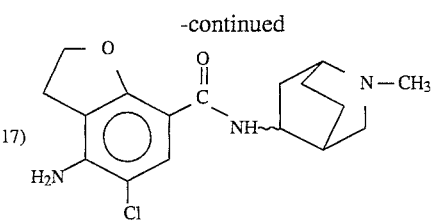

The process of the invention is characterized by easy and mild reaction conditions ensuring high yields and clean reaction products. It is known that when multiple substitutions are present on the benzene ring, they greatly limit the synthetic possibilities so obliging to long and tedious synthesis. We have found that the process of the invention is particularly useful also in those cases when multiple substitutions are present on the benzene ring, as is the case of most of the present formula (I) compounds. According to the new process of the invention, the compounds of formula (I) are prepared by A) reacting a compound of formula (II)

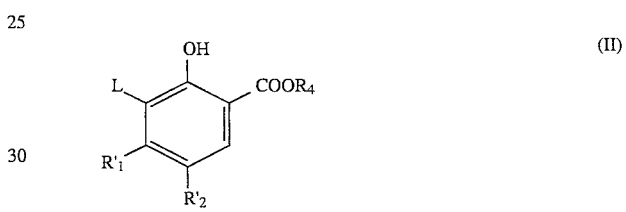

wherein
one of $R'_1$ and $R'_2$ is hydrogen or halogen and the other is amino, $C_2$–$C_4$ alkanoylamino or an otherwise protected amino group; L is a leaving group; and $R_4$ is hydrogen or a carboxy protecting group, with a compound of formula (III)

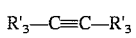

wherein one of the two $R'_3$ groups is hydrogen; linear or branched $C_1$–$C_4$ alkyl, $C_1$–$C_4$ alkoxy, or $C_2$–$C_4$ alkoxycarbonyl group; halogen; phenyl unsubstituted or substituted by a $C_1$–$C_4$ alkyl group; or a tri-$C_1$–$C_4$ alkyl silyl protecting group, and the other is, independently, hydrogen, halogen or a tri-$C_1$–$C_4$ alkylsilyl group, so obtaining a compound of formula (IV)

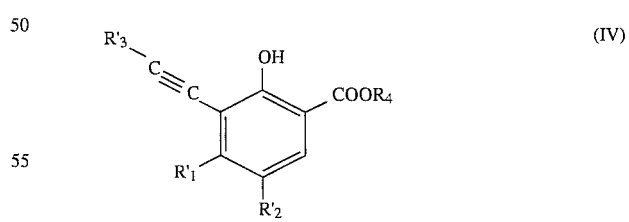

wherein $R'_1$, $R'_2$, $R'_3$ and $R_4$ are as defined above and, if desired, when $R'_3$ is a tri-$C_1$–$C_4$ alkylsilyl protecting group, removing it from the compound of formula (IV);

B) cyclizing a compound of formula (IV) and removing, if still present, the $R'_3$ group when it is a tri-$C_1$–$C_4$ alkyl silyl group, so obtaining a compound of formula (V)

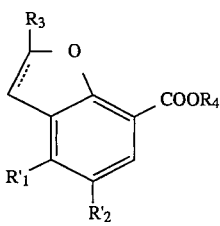

(V)

wherein $R'_1$, $R'_2$, $R_3$ and $R_4$ are as defined above and the symbol .... represents a double bond;

C) optionally reducing a compound of formula (V) wherein the symbol ... represents a double bond to give a corresponding compound of formula (V) wherein the symbol .... represents a single bond, and D) reacting a compound of formula (V) wherein $R'_1$, $R'_2$ and $R_3$ are as defined above, the symbol .... represents a double or a single bond and wherein $R_4$ is hydrogen, or a reactive derivative thereof, with a compound of formula (VI)

$H_2N—A$ (VI)

wherein A is as defined above and, as desired, after any of the steps B), C) and D), removing the amino protecting group possibly represented by one of $R_1'$ and $R_2'$, so obtaining a compound of formula (I), and, if desired reducing a compound of formula (I) wherein the symbol .... is a double bond to obtain a corresponding compound of formula (I) wherein the symbol .... is a single bond and/or, if desired, salifying a free compound of formula (I) or preparing a free compound of formula (I) from a salt thereof, and/or, if desired, separating a mixture of isomers of formula (I) into the single isomers.

When one of $R_1'$ and $R_2'$ is a $C_2$–$C_4$ alkanoylamino it is, e.g., acetyl or propanoyl. When one of $R'_1$ and $R'_2$ is an otherwise protected amino group, the amino protecting group may be, e.g., an aralkanoyl group such as, e.g., benzoyl; a $C_2$–$C_4$ alkoxycarbonyl group such as, e.g., t-butoxycarbonyl or an aralkoxycarbonyl group such as e.g., p-nitrobenzyloxycarbonyl. When one of $R'_1$ and $R'_2$ is a halogen atom it is the same halogen represented by one of $R_1$ and $R_2$ i.e., preferably chlorine or fluorine, in particular chlorine.

A leaving group L in a compound of formula (II) may be, e.g., an optionally substituted phenylsulphonate, such as, e.g., tosylate, brosylate, or p-fluorophenylsulphonate; an optionally substituted $C_1$–$C_4$ alkylsulphonate such as, e.g., mesylate or triflate; or a halogen atom such as, e.g., bromine or iodine.

When $R_4$ is a carboxy protecting group, it may be, e.g., a linear or branched chain $C_1$–$C_4$ alkyl, such as, e.g., methyl, ethyl or t-butyl; an aralkyl group such as, e.g., benzyl, p-nitrobenzyl or diphenylmethyl; or a trialkylsilyl group such as, e.g., trimethylsilyl or dimethyl-t-butylsilyl. Preferably $R'_1$ is amino or $C_2$–$C_4$ alkanoylamino and $R'_2$ is hydrogen or halogen, more preferably halogen, in particular chlorine.

Preferably the leaving group in a compound of formula (II) is halogen, more preferably bromine or iodine. Preferably $R_4$ is hydrogen or a linear or branched $C_1$–$C_4$ alkyl group, more preferably methyl.

The reaction between a compound of formula (II) and a compound of formula (III) may be performed in presence of a suitable catalyst such as, e.g., a group VIII metal, like palladium (Pd), and a copper Cu (I) salt, optionally operating, in a suitable organic solvent, in presence of an excess of an organic base, at a temperature of from about −40° to about 120° C., for a period of from about 1 hour to about 1 day.

A suitable catalyst may be, for instance, a metal chosen from group VIII, preferably a Pd(II) or Pd(0) catalyst with or without a ligand. Preferred ligands are: halides, acetates, or phosphor based ligands, such as, for instance $PPh_3$, $P(o\text{-}Tol)_3$, dppe or dppf.

A suitable copper Cu (I) salt may be, for instance, a salt which is commonly employed in the organic synthesis as a metalating agent, e.g. Cu(I) halide, $Cu_2O$, CuCN, or CuCN-LiCl complex, preferably CuI, CuCl or $Cu_2O$.

A suitable organic solvent may be, for instance, dimethylformamide (DMF), dioxane, tetrahydrofuran (THF), acetonitrile, dimethylsulfoxide or acetone; preferably DMF, THF or dioxane.

A suitable base may be, e.g., an organic base such as, for instance, an alkylamine, e.g. triethylamine ($Et_3N$) or diisopropylethylamine; or an arylalkylamine, e.g. benzylamine.

The cyclization of a compound of formula (IV) may be carried out operating in a suitable organic solvent, in presence of a suitable base at a temperature of from about −20° C. to about 200° C. to give a compound of formula (V) wherein the symbol .... represents a double bond.

A suitable organic solvent may be, for instance, an organic solvent such as, e.g., dimethylformamide (DMF), dioxane, tetrahydrofuran (THF), acetonitrile, dimethylsulfoxide, benzene, toluene or xylene.

A suitable base may be, for instance, an organic base such as a mono-, di- or tri- $C_1$–$C_4$ alkyl amine, preferably triethylamine; a $C_1$–$C_4$ alkyl substituted guanidine, preferably tetramethyl guanidine; an optionally substituted mono or dibasic phenylalkylamine; DBU, DBN, or DABCO, preferably DBU or DBN; an inorganic base such as, e.g., a base with an alkali metal, or an alkaline earth metal, e.g., $NaHCO_3$, $Na_2CO_3$, NaOH, $KHCO_3$, $K_2CO_3$ or KOH, preferably NaOH, $Na_2CO_3$, $K_2CO_3$ or KOH.

A particularly suitable base, may be, for example, the tetrabutylammonium fluoride, especially if appropriately supported, e.g., on silica gel. Using tetrabutylammonium as the base, there is, in fact, the additional advantage that, if a $C_1$–$C_4$ trialkylsilyl protecting group is still present on the compound of formula (IV), this is simultaneously removed during the cyclization reaction.

The cyclization of the compound (IV) may be also carried out directly on the crude of the reaction between the compound of formula (II) and the compound of formula (III), i.e. without preliminary purification of the compound (IV), e.g., operating in the presence of a suitable base, e.g. tetramethylguanidine, in a suitable organic solvent, e.g. toluene, at a temperature of, e.g. from about −20° C. to about 200° C.

Alternatively the cyclization may be performed "in situ", i.e. without isolating in any way the product of the reaction between the compound (II) and the compound (III) either as a crude or as purified product.

When the $R'_3$ group in a compound of formula (III) is a tri $C_1$–$C_4$ alkylsilyl protecting group, in particular a trimethylsilyl protecting group, it may be removed either before the above cyclization reaction or during the cyclization reaction or after the cyclization reacting by means of a suitable deprotecting agent, for example, an acidic deprotecting agent such as, e.g., PTS, a diluted aqueous mineral acid, gaseous HCl dissolved in an organic solvent, or silica gel; or a neutral deprotecting agent such as, e.g., KF in an aqueous medium or in a biphasic system or TBAF in an organic solvent, optionally in presence of an organic acid; a silver salt, such as, e.g., $AgNO_3$; or borax.

The optional reduction of a compound of formula (V) wherein the symbol ... represents a double bond to give a compound of formula (V) wherein the symbol ... represents a single bond may be, e.g., carried out in a suitable solvent, in a mono or biphasic system, in presence of a suitable heterogeneous or homogeneous catalyst and of a suitable hydrogen source at a temperature of from about −10 C. to about 100° C., for a period of from about one hour to about a few days.

A suitable solvent may be, for example, an organic solvent such as, e.g., acetone, acetic acid, an alcohol, e.g. methyl, ethyl or isopropyl alcohol, ethyl acetate, THF, DMF or a mixture thereof; an aqueous organic solvent mixture such as, e.g., alcohol/water, THF/water, acetic acid/water.

Preferred solvents may be, e.g. methanol, ethanol, acetic acid or acetone/ethyl acetate, acetic acid/methanol, acetic acid/ethanol, acetone/alcohol or acetic acid/acetone mixtures. A suitable catalyst may be, for example, a transition metal such as, e.g., a Pd, Pt, or Rh based catalyst, both in an heterogeneous or homogeneous system; preferably a Pd or Rh catalyst.

Suitable hydrogen sources may be, for example, molecular hydrogen, triethylammonium formate, cyclohexadiene, or trialkyl-tin hydride.

A reactive derivative of a compound of formula (V) wherein $R_4$ is hydrogen may be, for example, a corresponding halide, in particular the chloride, or the mixed anhydride with an appropriate carboxylic acid.

A preferred mixed anhydride is obtained reacting compound of formula (V) wherein $R_4$ is hydrogen with ethyl-chloroformate.

The reactive derivative of the compound (V) wherein $R_4$ is hydrogen includes also a corresponding $C_1$–$C_4$ alkyl ester; i.e., a compound of formula (V) wherein $R_4$ is $C_1$–$C_4$ alkyl.

The reaction between a compound of formula (V) or a reactive derivative thereof and a compound of formula (VI), may be carried out according to the known methods, described in the organic chemistry for the amidation reactions following conventional procedures, for example those described in U.S. Pat. No. 4,888,353.

For example the reaction between the compound of formula (V) wherein $R_4$ is hydrogen and the compound of formula (VI) may be carried out operating in a suitable organic solvent, such as, e.g., methylene chloride or dimethyl-formamide, in the presence of N,N-carbonyldiimidazole.

The removal of the amino protecting groups possibly present, after the reaction steps B), C) and D), may be carried out according known procedures.

The optional reduction of a compound of formula (I) wherein the symbol .... is a double bond to give a corresponding compound of formula (I) wherein the symbol .... is a single bond may be carried out according to known methods, following conventional reaction conditions, for example, using the same reaction conditions and reagents, described before for the operational reduction of a compound of formula (V) wherein the symbol .... is a double bond.

The optional salification of a free compound of formula (I), the optional preparation of a free compound of formula (I) from a salt thereof, and the optional separation of a mixture of isomers of formula (I) into the single isomers, may be carried out in a conventional way, following the known and usual procedures of the organic chemistry.

The compounds of formula (II), (III), and (VI) are known compounds or may be prepared by known methods from known compounds.

For example, a compound of formula (VI) wherein the A is 2-pyrrolidinyl methyl may be prepared following the procedure described in UK patent No. 1,481,251 or in U.S. Pat. No. 4,888,353; a compound of formula (VI) wherein the group A is endo-8-methyl-8-azabicyclo[3.2.1]oct-3-yl, i.e. endo-8-methyl-8-azabicyclo[3.2.1]octan-3-amine may be prepared following the procedure described in Archer S., Lewis T., Unser M.J.Am.Chem.Soc. 1987, 79, 4194; and a compound of formula (VI) wherein the group A is endo-9-methyl-9-azabicyclo[3.3.1]non-3-yl, i.e. endo-9-methyl-9-azabicyclo[3.3.1]nonan-3-amine, may be prepared following the procedure described in Hadley M., EP 13.138, 1979, Chem. Abstract 1981, 94, 65477 or Donatch P., Engel G., Uegi B. Richardson B., Stadler P., GB 2,125,398, 1984.

The compounds of formula (I) are $5HT_3$ receptor antagonists and can be useful, for example, in the treatment of CNS disorders such as, e.g., anxiety and psychosis, and/or in the treatment of gut motility disorders and/or emesis.

The compounds of the invention can be also useful, for example as cognition activators.

The compounds of the invention may be administered in a variety of dosage from, e.g., orally in the form of tablets, pills, capsules, suspensions, drops or syrups; parenterally, e.g., intravenously, intramuscularly as solutions or suspensions, or by subcutaneous administration.

The pharmaceutical compositions containing the compounds of the invention may be prepared in a conventional way by employing conventional carriers or diluents.

Conventional carriers or diluents are, for example, water, gelatine, lactose, starches, magnesium stearate, talc, vegetable oils, cellulose and the like.

Tablets, pills and capsules may e.g., contain a binder such as, e.g., gum tragacanth; excipients such as, e.g., dicalcium phosphate; a disintegrating agent such as, e.g., corn starch, a lubricant such as, e.g., magnesium stearate; a sweetening agent such as, e.g., sucrose or a flavouring agent such as cherry flavouring.

Suitable pharmaceutical forms for parenteral use are sterile aqueous solutions or dispersions and sterile powders for the extemporaneous preparations.

The dosage of the present compounds, either for prophylaxis or therapeutic treatment, will depend on the chosen route of administration, on the particular compound chosen, on the particular patient under treatment and also on the nature and severity of the disorder.

A suitable therapeutically effective dosage may be, for example, included within the range of about 0.010 to about 20 mg/kg of body weight.

Preferably the compounds may be, e.g., administered in single or divided doses such that the total daily dosage falls within the range of about 0.020 to about 10 mg/kg per day.

The meaning of the abbreviations used in the present specification is as follows:

$PPh_3$=triphenylphosphine, $P(O-Tol)_3$=tri(orto)tolylphosphine, dppf=1,1-bis(diphenylphosphino)ferrocene, dppe=1,2-bis(diphenylphosphino)ethane, BDU=1,8-diazabicyclo[5.4.0]undec-7-ene, DBN=1,5-diazabicyclo[4,3,0]non-5-ene, DABCO=1,4-diazabicyclo[2.2.2]octane, PTS=p-toluenesulfonic acid and TBAF=tetrabutylammonium fluoride.

The following examples illustrate the preparation of the intermediates and compounds of the present invention. These examples are illustrative only and are not intended to limit the scope of the invention in any way.

EXAMPLE 1

Preparation of the Starting Materials

Step 1

Methyl 4-acetamido-5-chloro-salicylate

Method A

Chlorine (ca. 3 g) was passed through a solution of methyl 4-acetamido-salicylate (5 g) in acetic acid (200 ml). The solution was then poured in water (500 ml). After 30 minutes stirring, the precipitated was filtered and washed with water until neutrality. After crystallization from MeOH the title product was obtained as a white solid (4.4 g).

Method B

To a solution of methyl 4-acetamido-salicylate (10 g) in acetic acid (200 ml) and 15% HCl (50 ml), sodium chlorate (1.95 g) was added.

After one hour stirring, water was added (200 ml), and after further 30 minutes stirring, the precipitated solid was filtered, washed with water and crystallized from EtOH, to yield the title product (7.1 g).

Step 2 methyl 3-iodo-4-acetamido-5-chloro-salicylate

To a solution of methyl 4-acetamido-5-chloro-salicylate (2 g) in $CH_2Cl_2$ (200 ml) and absolute MeOH (80 ml), $NaHCO_3$ (1.66 g) and $BTMAICl_2$(Benzyltrimethylammonium iododichloride, 2.8 g) were sequentially added, and the mixture was stirred overnight at 25° C.

The solvent was removed in vacuo, and the residue was taken-up with $CH_2Cl_2$ (440 ml). The organic phase was washed with diluted HCl, Na thiosulphate, and water, separated, and dried over anhydrous sodium sulphate.

Most of the solvent was removed in vacuo, and the precipitated white solid was filtered to yield 2.57 g of the title compound.

EXAMPLE 2

Methyl 4-acetamido-5-chloro-benzo[b]furan-7-carboxylate

Method A

To a solution of methyl 3-iodo-4-acetamido-5-chlorosalicylate (2 g) in distilled $Et_3N$ (60 ml) and dioxane (40 ml), trimethylsilylacetylene (1 ml), CuI (23 mg), and $PdCl_2(PPh_3)_2$ (152 mg) were added. The reaction mixture was stirred at 40° C. for 1.5 hours, after which time the solvents were removed in vacuo. A sample of the residue was purified by column chromatography for analytical purposes eluting with diethyl ether/hexane mixtures to yield the intermediate methyl 3-trimethylsilylethynyl-4-acetamido-5-chloro-salic ylate.

NMR ($CDCl_3$) δ ppm: 2.19 (3H, s); 3.96 (3H,s); 7.14 (1H, br.s); 7.87 (1H, s); 11.28 (1H, s). GC-Mass (EI): 339 ($M^+$.), 324 (M-Me), 304 (M-Cl).

The crude was instead taken up with toluene (160 ml) and to the solution heated to reflux, tetramethylguanidine (1.36 ml) and silica gel (4 g) were added. The mixture was refluxed for further two hours, cooled to room temperature and filtered. The filtrate was discarded and the silica gel was carefully washed with boiling acetone. The filtrate was evaporated in vacuo to yield 0.92 g of the title product.

NMR ($CDCl_3$) δ ppm: 2.31 (3H, s); 3.99 (3H, s); 6.85 (1H, d, J=2.3 Hz); 7.57 (1H, br.s); 7.71 (1H, s, J=2.3 HZ); 8.0 (1H, s). GC-Mass (EI); 267 ($M^+$.), 225 ($M-CH_3CO$).

Method B

The reaction was performed as in method A except that only tetramethylguanidine was added. The mixture was refluxed for 2 hours.

A sample of this solution was purified by column chromatography for analytical purposes to yield the 2-trimethylsilyl derivative of methyl 4-acetamido-5-chloro-benzo[b]furan-7-carboxylate.

NMR ($CDCl_3$) δ ppm: 0.36 (9H, s); 2.29 (3H), s); 3.97 (3H,s); 6.96 (1H, s); 7.58 (1H, br.s); 7.94 (1H, s). GC-Mass (EI); 341 (M+2), 339 ($M^+$.), 304 (M-Cl), 297 ($M-CH_3CO$), 282 (297-MeOH).

Silica gel was then added and the refluxing was continued for further 3 hours. After cooling, the mixture was worked up as described in method A. The title product was so obtained in 65% yield.

Method C

The reaction was performed as described in method A and the intermediate methyl 3-trimethylsilylethynyl-4-acetamido-5-chlorosalicylate was isolated by column chromatography and desilylated according to literature (e.g. Using $AgNO_3$, KCN, EtOH, according to Rec.Trav.Chim. 86, 1138, 1967) to yield methyl 3-ethynyl-4-acetamido-5-chloro-salicylate.

NMR ($CDCl_3$) δ ppm: 2.2 (3H, s); 3.6 (1H,s); 3.9 (3H, s); 7.2 (1H, br.s); 7.9 (1H,s); 11.3 (1H,s). Mass(EI): 267 ($M^+$.); 232 (M-Cl).

To a solution of the above product (267 mg) in MeOH (2 ml) $Na_2CO_3$ (105 mg) was added. The mixture was heated at 35° C. for 3 hours. The mixture was poured in $CH_2Cl_2$.

The organic phase was separated, dried and evaporated in vacuo. The title product was so obtained. It was in any respect identical to the product of methods A and B.

Method D

The reaction was performed as in method C except that the intermediate methyl 3-trimethylsilylethynyl-4-acetamido-5-chloro-salicylate was precipiatated by dilution with hexane of the reaction solution. The above product was dissolved in toluene, heated to reflux and an equal amount of silica gel supported tetrabutylammonium fluoride (1.1 mmole of fluoride per gram) was added. Refluxing was continued for 10 minutes. The reaction mixture was then filtered, and, upon cooling, the title product was collected by filtration in 82% yield (3.3 g from 5 g of starting material).

EXAMPLE 2A

Methyl 4-acetamido-5-chloro-benzo(b)furan-7-carboxylate

To a solution of methyl 3-iodo-4-acetamido-5-chloro salicylate (0.25 g) in 1,1,3,3-tetramethylguanidine (10 ml) and dioxane (10 ml), (trimethylsilyl) acetylene (0.1 ml), CuI (10 mg), and $PdCl_2(PPh_3)_2$ (19 mg) were added. The reaction mixture was stirred at 50°–60° C. under argon overnight. The solution was poured in $CH_2Cl_2$/10% HCl, and the organic phase was washed with water, dried over anhydrous $Na_2SO_4$, and evaporated under vacuum. After column chromatography the title product was obtained as a white solid (0.13 g, 72%). The compound was identical to a sample of the product obtained according to example 2.

EXAMPLE 3

Methyl 4-acetamido-5-chloro-2,3-dihydrobenzo[b]furan-7-carboxylate

A solution of methyl-4-acetamido-5-chloro-benzo[b]furan-7-carboxylate (0.5 g) in acetone (300 ml) was stirred for 3 hours in presence of 5% Rh/C (0.5 g) in a hydrogen atmosphere. The catalyst was filtered off and the filtrate was evaporated in vacuo to yield 0.48 g of the title product.

NMR (CDCl$_3$) ppm: 2.21 (3H, s) 3.17 (2H, t, J=8.8 Hz); 3.86 (3H,s); 4.70 (2H, t, J=8.8 Hz); 7.45 (1H, br.s); 7.70 (1H,s). GC-Mass (EI): 269 (M$^+$.), 234 (M-Cl), 196 (M-MeOH-CH$_3$CO).

EXAMPLE 4

The reaction was carried out as described in example 2 except that Rh/Al$_2$O$_3$ was used to yield, after work-up the product described in example 2 in 90% yield.

EXAMPLE 5

The reaction was carried out as described in example 2 except that acetic acid/methanol and Pd/C were used instead to yield, after work-up, the product described in example 2 and 3 in 62% yield.

EXAMPLE 6

Methyl 4-acetamido-5-chloro-2-phenyl-benzo[b]furan-7-carboxylate

Methyl 3-iodo-4-acetamido-5-chloro-salicylate was reacted with phenylacetylene in analogy to what described in Example 1, Method A and B, except that no SiO$_2$ was added. After column chromatography the title product was obtained.

By proceeding analogously the following products can be obtained starting from the appropriate acetylene derivative:

methyl 4-acetamido-5-chloro-2-methyl-benzo[b]furan-7-carboxylate;

methyl 4-acetamido-5-chloro-2-ethyl-benzo[b]furan-7-carboxylate;

methyl 4-acetamido-5-chloro-2-chloro-benzo[b]furan-7-carboxylate;

methyl 4-acetamido-5-chloro-2-ethoxy-benzo[b]furan-7-carboxylate;

methyl 4-acetamido-5-chloro-2-methoxy-benzo[b]furan-7-carboxylate;

methyl 4-acetamido-5-chloro-2-(4-methoxy)phenyl-benzo[ b]furan-7-carboxylate.

EXAMPLE 7

(S)-4-amino-5-chloro-N-(2-pyrrolidinyl-methyl)-2,3-dihydrobenzo[ b]furan-7-carboxamide.HCl To a stirred suspension of 4-amino-5-chloro-2,3-dihydrobenzo[ b]furan-7-carboxylic acid (1.42 g; 0.0066 mole) in 30 ml of methylene chloride kept under nitrogen atmosphere (1.08 g; 0.0066 mole) N,N-carbonyldiimidazole is added. After 3 hours, the mixture is cooled to −20° C. and a solution of (S)-2-aminomethylpyrrolidine, (0.66 g; 0.0066 mole) in 1 ml of methylene chloride is added dropwise.

After 6 hours, the reaction mixture is filtered and washed twice with 20 ml of 1N NaOH. The organic layer is dried over anhydrous sodium sulfate. After filtration a solution of hydrochloric acid in 2-propanol is added while cooling at 0°–5° C. The precipitate is collected on a filter, washed with methylene chloride, and recrystallized from water/2-propanol to yield 1.4 g of the title product.

By analogous procedure the following compounds can be also prepared:

5-amino-N-[2-(1-ethyl)-pyrrolidinyl-methyl]-2,3-dihydrobenzo[ b]furan-7-carboxamide.HCl;

5-acetylamino-N-[2-(1-ethyl)-pyrrolidinyl-methyl]-2,3-dihydrobenzo[ b]furan-7-carboxamide.HCl;

2-methyl-4-chloro-5-amino-N-[2-(1-ethyl)-pyrrolidinylmethyl]- 2,3-dihydrobenzo[b]furan-7-carboxamide.HCl;

4-amino-5-chloro-N-[2-(1-ethyl)-pyrrolidinyl-methyl]-2,3-dihydrobenzo[ b]furan-7-carboxamide.HCl;

4-amino-5-chloro-N-[(1,2-diethyl)-pyrazolidin-3-yl]-2,3-dihydrobenzo[ b]furan-7-carboxamide.HCl;

4-acetylamino-5-chloro-N-[2-(1-ethyl)-pyrrolidinyl-methyl]- 2,3-dihydrobenzo[b]furan-7-carboxamide.HCl;

5-amino-N-(2-pyrrolidinyl-methyl)-2,3-dihydrobenzo[b]furan- 7-carboxamide.HCl;

4-acetylamino-N-[2-(1-ethyl)-pyrrolidinyl-methyl]- 2,3-dihydrobenzo[b]furan-7-carboxamide.HCl;

4-chloro-5-amino-N-[2-(1-ethyl)-pyrrolidinyl-methyl]-2,3-dihydrobenzo[b]furan-7-carboxamide.HCl 4-amino-N-[2-(1-ethyl)-pyrrolidinyl-methyl]-2,3-dihydrobenzo[ b]furan-7-carboxamide.HCl.

EXAMPLE 8

4-amino-5-chloro-N-(endo-8-methyl-8-azabicyclo [3.2.1]oct-3-yl-)-2,3-dihydrobenzo[b]furan-7-carboxamide.HCl To a stirred solution of 4-amino-5-chloro-2,3-dihydrobenzo[b] furan-7-carboxylic acid (2.13 g; 0.010 mole) in 30 ml of anhydrous dimethylformamide is added N,N-carbonyldiimidazole (1.96 g; 0.012 mole).

Nitrogen is bubbled into the solution and stirring at room temperature continued overnight, followed by dropwise addition of a solution of endo-8-methyl-8-azabicyclo[3.2.1] octan-3-amine, (1.40 g; 0.010 mole), in 5 ml of anhydrous dimethylformamide. The reaction mixture is heated at 70° C. for 18 hours, cooled, poured into water and extracted with methylene chloride. The organic layer is washed twice with a sodium bicarbonate solution and dried over anhydrous sodium sulfate. The solution is filtered, evaporated to dryness and the product purified by flash-chromatography (SiO$_2$)(CH$_2$Cl$_2$-MeOH-NH$_4$OH 30%, 80:20:1, as eluant), followed by treatment with a solution of hydrochloric acid in ethanol: the solid obtained is recovered by filtration and recrystalized in ethanol to yield 1.6 g of the title product.

EXAMPLE 9

The following compounds can be also prepared from the corresponding carboxylic acid and the appropriate amine according to the procedure of example 8:

4-amino-5-chloro-N-(endo-9-methyl-9-azabicyclo[3.3.1] non-3-yl)- 2,3-dihydrobenzo[b]furan-7-carboxamide.HCl;

4-amino-5-chloro-N-(1-azabicyclo[4.4.0]dec-4-yl)-2,3- dihydrobenzo[b]furan-7-carboxamide.HCl;

4-amino-5-chloro-N-(1-azabicyclo[3.3.1]non-4-yl)-2,3-dihydrobenzo[b]furan-7-carboxamide.HCl;

4-amino-5-chloro-N-(2-methyl-2-azabicyclo[2.2.2]oct-5-yl)-2,3-dihydrobenzo[b]furan-7-carboxamide.HCl;

4-amino-5-chloro-N-(1-azabicyclo[2.2.2]oct-3-yl)-2,3-dihydrobenzo[b]furan-7-carboxamide.HCl.

EXAMPLE 10

Tablets each weighing 150 g and containing 60 mg of the active substance can be manufactured by blending and compressing the following ingredients:

| | |
|---|---|
| 4-amino-5-chloro-N-(endo-8-methyl-8-azabicyclo[3.2.1]oct-3-yl)-2,3-dihydrobenzo[b]furan-7-carboxamide hydrochloride | mg 60 |
| Starch | mg 50 |
| Cellulose microcrystalline | mg 30 |
| Polyvinylpyrrolidone | mg 5 |
| Sodium carboxymethyl starch | mg 4,5 |
| Magnesium stearate | mg 0.5 |

EXAMPLE 11

Capsules, each dosed at 200 mg and containing 80 mg of the active substance can be prepared as follows:

| | |
|---|---|
| 4-amino-5-chloro-N-(endo-8-methyl-8-azabicyclo[3.2.1]oct-3-yl)-2,3-dihydrobenzo[b]furan-7-carboxamide hydrochloride | mg 80 |
| Corn starch | mg 60 |
| Cellulose Microcrystalline | mg 59 |
| Magnesium stearate | mg 1 |

This formulation can be encapsulated in two-piece hard gelatin capsules and dosed at 200 mg for each capsule.

We claim:

1. A process for the preparation of a compound of the following formula (I)

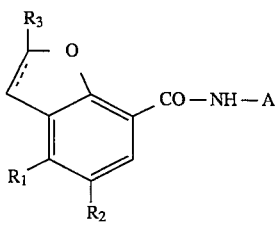

wherein
one of $R_1$ and $R_2$ is hydrogen or halogen and the other is independently, an amino group or a $C_2-C_4$ alkanoyl amino group; $R_3$ is hydrogen; a linear or branched $C_1-C_4$ alkyl, $C_1-C_4$ alkoxy or $C_2-C_4$ alkoxycarbonyl group; halogen; or phenyl unsubstituted or substituted by a $C_1-C_4$ alkyl group; A is a group —$(CH_2)_n$-Het wherein Het is an optionally substituted heteromonocyclic or heterobicyclic ring containing one or two nitrogen atoms and n is zero or an integer of 1 to 3; and the symbol .... represents a single or double bond, and the pharmaceutically acceptable salts thereof, said process comprising:

A) reacting in the presence of a catalytic amount of a catalyst containing a metal of group VIII of the periodic table, a compound of formula (II)

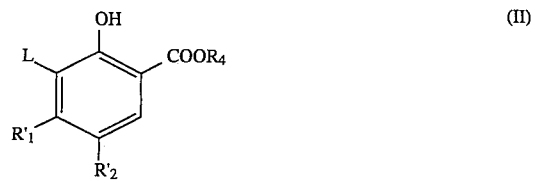

wherein
one of $R'_1$ and $R'_2$ is hydrogen or halogen and the other is amino, $C_2-C_4$ alkanoylamino or an otherwise protected amino group; L is a leaving group; and $R_4$ is hydrogen or a carboxy protecting group, with a compound of formula (III)

wherein one of the two $R'_3$ groups is hydrogen; a linear or branched $C_1-C_4$ alkyl, $C_1-C_4$ alkoxy or $C_2-C_4$ alkoxycarbonyl group; halogen; phenyl unsubstituted or substituted by a $C_1-C_4$ alkyl group; or a tri-$C_1-C_4$ alkylsilyl protecting group, and the other is, independently, hydrogen, halogen or tri-$C_1-C_4$ alkylsilyl group, so obtaining a compound of formula (IV)

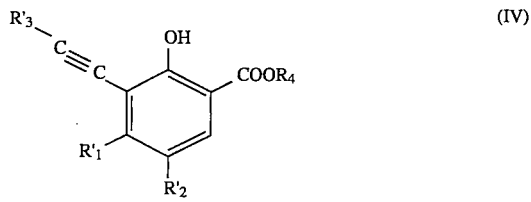

wherein $R'_1$, $R'_2$, $R'_3$ and $R_4$ are as defined above, and, if desired, when $R'_3$ is a tri-$C_1-C_4$ alkylsilyl protecting group, removing it from the compound of formula (IV);

B) cyclizing a compound of formula (IV) and removing, if still present, the $R'_3$ group when it is tri-$C_1-C_4$ alkylsilyl protecting group, so obtaining a compound of formula (V)

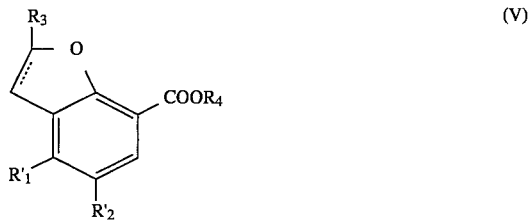

wherein $R'_1$, $R'_2$, $R_3$ and $R_4$ are as defined above and the symbol .... represents a double bond;

C) optionally reducing a compound of formula (V) wherein the symbol .... represents a double bond so obtaining a compound of formula (V) wherein the symbol .... represents a single bond, and D) reacting a compound of formula (V) wherein $R'_1$, $R'_2$ and $R_3$ are as defined above, the symbol .... represents a single or a double bond, and wherein $R_4$ is hydrogen or a reactive derivative thereof with a compound of formula (VI)

wherein A is as defined above and, as desired, after any of the steps B), C) and D) removing the amino protecting group possibly represented by one of $R_1'$ and $R^{2'}$, so obtaining a compound of formula (I), and, if desired, reducing a compound of formula (I) wherein the symbol .... is a double bond to obtain a corresponding compound of formula (I) wherein the symbol .... is a single bond and/or if desired, salifying a free compound of formula (I), or, if desired, obtaining a free compound of formula (I) from a salt thereof and/or, if desired, separating a mixture of isomers of formula (I) into the single isomers.

2. A process for preparing a compound of formula (V)

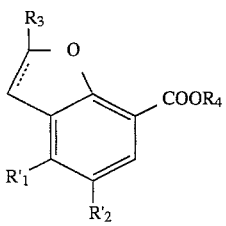

(V)

wherein
one of $R'_1$ and $R'_2$ is hydrogen or halogen and the other is amino, $C_2$–$C_4$ alkanoylamino or an otherwise protected amino group; $R_3$ is hydrogen; a linear or branched $C_1$–$C_4$ alkyl, $C_1$–$C_4$ alkoxy or $C_2$–$C_4$ alkoxycarbonyl group; halogen; or phenyl unsubstituted or substituted by a $C_1$–$C_4$ alkyl group; $R_4$ is hydrogen or a carboxy protecting group, and the symbol .... is a single or double bond, said process comprising A) reacting a compound of formula (II)

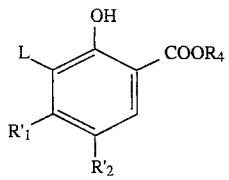

(II)

wherein
$R'_1$, $R'_2$ and $R_4$ are as defined above and L is a leaving group, with a compound of formula (III)

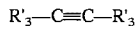

$R'_3$—C≡C—$R'_3$ (III)

wherein one of the two $R'_3$ groups is hydrogen; a linear or branched $C_1$–$C_4$ alkyl, $C_1$–$C_4$ alkoxy or $C_2$–$C_4$ alkoxycarbonyl group; halogen; phenyl unsubstituted or substituted by a $C_1$–$C_4$ alkyl group; or a tri-$C_1$–$C_4$ alkylsilyl protecting group, and the other is, independently, hydrogen, halogen, or a tri-$C_1$–$C_4$-alkylsilyl group, so obtaining a compound of formula (IV)

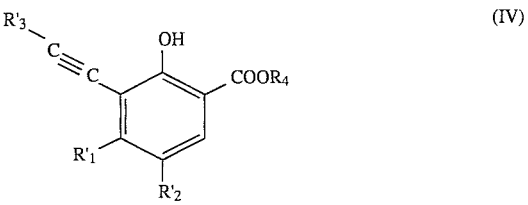

(IV)

wherein $R'_1$, $R'_2$, $R'_3$ and $R_4$ are as defined above and, if desired, when $R'_3$ is a tri-$C_1$–$C_4$ alkylsilyl protecting group removing it from the compound of formula (IV); and B) cyclizing a compound of formula (IV) and removing, if still present, the $R'_3$ group when it is tri-$C_1$–$C_4$ alkyl silyl protecting group; and C) optionally reducing a compound of formula (V) wherein the symbol .... represents a double bond to give a corresponding compound of formula (V) wherein the symbol .... represents a single bond.

3. A method of treating a cognitive disorder in a patient in need of such treatment, which comprises administering to said patient an effective amount of a compound of formula (I):

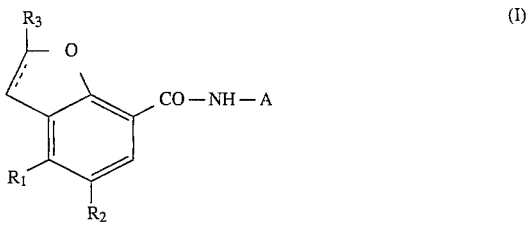

(I)

wherein one of $R_1$ and $R_2$ is hydrogen or halogen and the other is, independently, an amino group or a $C_2$–$C_4$ alkanoyl amino group; $R_3$ is hydrogen; a linear or branched $C_1$–$C_4$ alkyl, $C_1$–$C_4$ alkoxy or $C_2$–$C_4$ alkoxycarbonyl group; halogen; or phenyl unsubstituted or substituted by a $C_1$–$C_4$ alkyl group; A is a group —$(CH_2)_n$-Het wherein Het is an optionally substituted heteromonocyclic or heterobicyclic ring containing one or two nitrogen atoms, and n is zero or an integer of 1 to 3; and the symbol .... represents a single or double bond, or a salt or isomer thereof.

4. The process according to claim 1, in which $R'_1$ is amino or $C_2$–$C_4$ alkanoylamine, and $R'_2$ is hydrogen or halogen.

5. The process according to claim 1, in which $R'_1$ is a protected amino group and $R'_2$ is hydrogen or halogen.

* * * * *